United States Patent
Chopard

(10) Patent No.: US 8,561,608 B2
(45) Date of Patent: Oct. 22, 2013

(54) FLUID PRODUCT INHALER WITH DEVICE FOR OPENING RESERVOIR CONTAINING FLUID PRODUCT

(75) Inventor: David Chopard, Autheuil Authouillet (FR)

(73) Assignee: Aptar France SAS, Le Neubourg (FR)

( * ) Notice: Subject to any disclaimer, the term of this patent is extended or adjusted under 35 U.S.C. 154(b) by 626 days.

(21) Appl. No.: 12/667,344

(22) PCT Filed: Jul. 1, 2008

(86) PCT No.: PCT/FR2008/051222
§ 371 (c)(1),
(2), (4) Date: Dec. 30, 2009

(87) PCT Pub. No.: WO2009/007640
PCT Pub. Date: Jan. 15, 2009

(65) Prior Publication Data
US 2010/0192950 A1    Aug. 5, 2010

(30) Foreign Application Priority Data
Jul. 3, 2007   (FR) ...................................... 07 56237

(51) Int. Cl.
*A61M 16/00* (2006.01)
(52) U.S. Cl.
USPC ................................ 128/203.15; 128/203.21
(58) Field of Classification Search
USPC ............. 128/203.12, 203.15, 203.21–203.24; 604/86–88
See application file for complete search history.

(56) References Cited

U.S. PATENT DOCUMENTS

2006/0048780 A1    3/2006   Burr et al.

FOREIGN PATENT DOCUMENTS

| DE | 197 57 208 A1 | | 6/1999 |
|---|---|---|---|
| GB | 2 420 982 A | | 6/2006 |
| WO | 2005/037353 A1 | | 4/2005 |
| WO | WO 2005/037353 | * | 4/2005 |
| WO | 2006/062651 A1 | | 6/2006 |
| WO | WO 2006/062651 | * | 6/2006 |
| WO | 2006/079750 A1 | | 8/2006 |

* cited by examiner

*Primary Examiner* — Theodore Stigell
(74) *Attorney, Agent, or Firm* — Sughrue Mion, PLLC

(57) ABSTRACT

An inhaler device having an opening device for opening an individual reservoir containing a single dose of fluid, such as powder, the reservoir including a closure wall, the opening device having hollow perforator mechanism that is adapted to perforate the closure wall of the reservoir, the hollow perforator mechanism being connected to an expulsion channel so as to transport the powder towards a dispenser orifice of the inhaler. The opening device includes at least one air channel connected to the expulsion channel, such that during inhalation, an air flow passing through the at least one air channel mixes, in the expulsion channel, with the air and powder flow leaving the reservoir through the hollow perforator mechanism. The air channel is formed by a through hole made in a wall of the perforator mechanism, the through hole being oriented substantially parallel to the expulsion channel.

13 Claims, 2 Drawing Sheets

FLUID PRODUCT INHALER WITH DEVICE FOR OPENING RESERVOIR CONTAINING FLUID PRODUCT

The present invention relates to a reservoir opening device and to a fluid dispenser device, more particularly a dry-powder inhaler, including such an opening device.

Dry-powder inhalers are well known in the prior art. Various kinds exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. Obviously however, the inhaler is more difficult to use, since the user is obliged to load a capsule into the inhaler before each use. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. In a variant, it has been proposed to perforate the closure layer or wall. That can present the drawback that cut wall-portions run the risk of retaining a fraction of the dose inside the reservoir, so that metering accuracy and reproducibility are thus not guaranteed. Another problem with perforation is to guarantee an inhalation flow that is sufficient to expel the powder from the perforated blister and to transport it to the dispenser orifice. Documents WO 2006/079750, WO 2005/037353, and DE 19757208 describe prior-art perforator devices.

An object of the present invention is to provide a reservoir opening device and a fluid dispenser device, in particular a dry-powder inhaler, that do not have the above-mentioned drawbacks.

In particular, an object of the present invention is to provide such devices that are simple and inexpensive to manufacture and to assemble, that are reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that are as compact as possible, while guaranteeing sealing and absolute integrity of all of the doses up to their expulsion.

Another object of the present invention is to provide such devices for which the variability between emitted doses is reduced.

The present invention thus provides an inhaler device comprising an opening device for opening an individual reservoir containing a single dose of fluid, such as powder, said reservoir including a closure wall, said opening device comprising hollow perforator means that are adapted to perforate said closure wall of the reservoir, said hollow perforator means being connected to an expulsion channel so as to transport the powder towards a dispenser orifice of said inhaler, said opening device including at least one air channel connected to said expulsion channel, such that during inhalation, an air flow passing through said at least one air channel mixes, in said expulsion channel, with the air and powder flow leaving the reservoir through said hollow perforator means, said at least one air channel being formed by a through hole made in a wall of said perforator means, said at least one through hole being oriented substantially parallel to said expulsion channel.

Advantageously, said at least one air channel is made in a wall of the perforator means that does not penetrate into the reservoir.

Advantageously, said at least one air channel is substantially rectilinear.

Advantageously, said at least one air channel has a section that is substantially constant along its length.

In a variant, said at least one air channel has a section that varies along its length.

Advantageously, said perforator means include two opposite perforator ends that are spaced apart by a distance.

Advantageously, said perforator means include two air channels that are disposed symmetrically between said two perforator ends.

Advantageously, the flow of incoming air penetrates into the open reservoir over the outside of said perforator means.

Advantageously, said perforator means include at least one external projection, such as a spline, so as to form at least one passage for the incoming air entering into the open reservoir.

Advantageously, said opening device is activated by the user inhaling.

Advantageously, during inhalation, a reservoir is moved against said opening device, such that said reservoir is opened while a first inhalation flow enters into the reservoir by passing over the outside of said perforator means, causing the fluid to be expelled towards the expulsion channel by passing into said perforator means, said first inhalation flow mixing, in the expulsion channel, with a second inhalation flow passing through said at least one air channel.

Advantageously, said opening device does not move relative to the body of the inhaler while the reservoir is being opened.

Advantageously, the reservoirs are made in the form of an elongate strip comprising a plurality of individual reservoirs disposed one behind another.

These characteristics and advantages and others of the present invention appear more clearly from the following detailed description of several embodiments and variants thereof, given by way of non-limiting example, and with reference to the accompanying drawings, and in which.

With reference to the figures, the invention mainly relates to an opening device for opening individual reservoirs for a dry-powder inhaler. It applies in particular to inhalers in which the reservoirs 20 are formed by blisters that are disposed one behind another on a flexible strip (not shown). Each reservoir or blister 20 includes a leaktight closure wall 21 and contains a dose of powder. Advantageously, on each actuation, the strip unwinds progressively, an indexer wheel (not shown) being provided both to cause the strip to advance, and to receive a blister to be opened, on each actuation. Advantageously, the invention applies in particular to an inhaler in which said indexer wheel is movable not only in turning, but also towards perforator means 40 that do not move relative to the body of the inhaler. Naturally, other applications can be envisaged.

Figure 4:
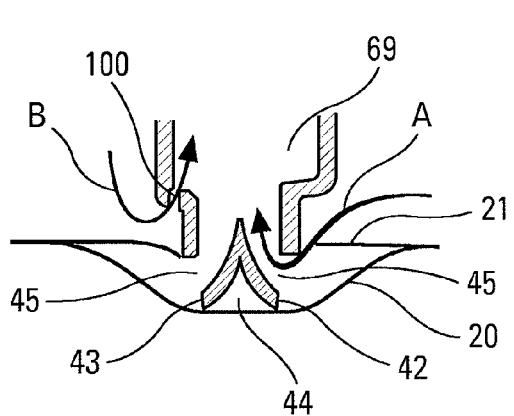
FIGS. 4 to 6 are diagrammatic views of variant embodiments of a perforator element.
Figure 5:
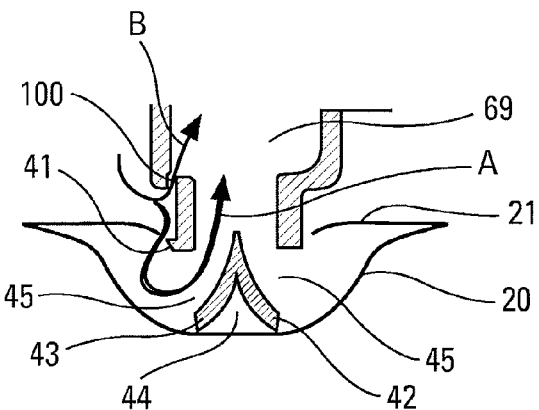
Figure 6:
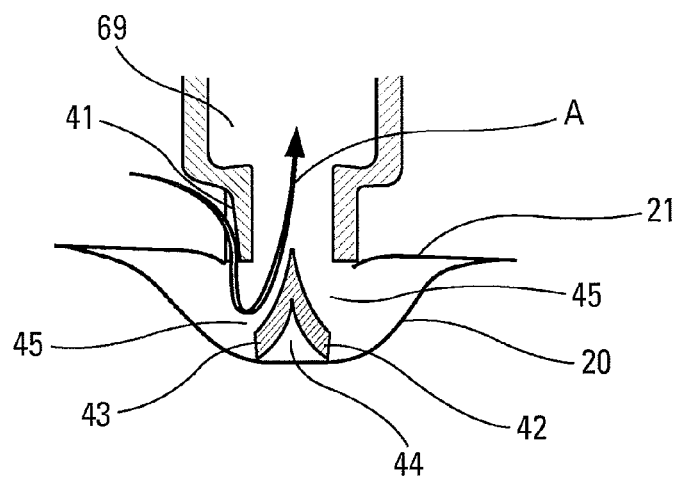

The opening device includes perforator means (or perforator elements) 40 that are adapted to perforate the closure wall 21 of a blister 20 on each actuation. The perforator element 40 is hollow and defines an expulsion channel 69. It includes at least one perforator end, preferably two perforator ends 42, 43. The perforator ends perforate the closure wall 21 and penetrate into the blister. Each perforator end 42, 43 includes an opening 45 enabling the powder to be expelled from the blister, so as to be transported into the expulsion channel. Preferably, the opening device is triggered by the user inhaling, and the inhalation flow penetrates into the open blister, mixes with the powder, and drives it towards the expulsion channel through the opening(s) 45 of the perforator end(s) 42, 43. Preferably, the inhalation flow penetrates into the open blister by passing over the outside of the perforator element 40, as shown by arrow A in FIGS. 4 to 6.

In the invention, the opening device includes at least one air channel 100 that is also connected to the expulsion channel 69, and through which there flows an air flow (arrow B) that, during inhalation, mixes in the expulsion channel 69 with the air and powder flow (arrow A) being expelled from the blister 20 and passing into the hollow perforator element 40. The air flow thus promotes effective and reliable transport of the powder expelled from the blister to the dispenser orifice 1 of the inhaler. It also makes it possible to reduce the variability between emitted doses. The air channels 100 formed in the perforator element 40 are elements of shapes that can be reproduced industrially by molding, thereby making it possible to stabilize performance and the fluid-flow parameters. In particular, the flow B (of dimensions that can be determined in industrial manner) can be sufficiently preponderant compared to the main flow A (more difficult to determine), to enable the overall variability of performance to be reduced.

Figure 1:
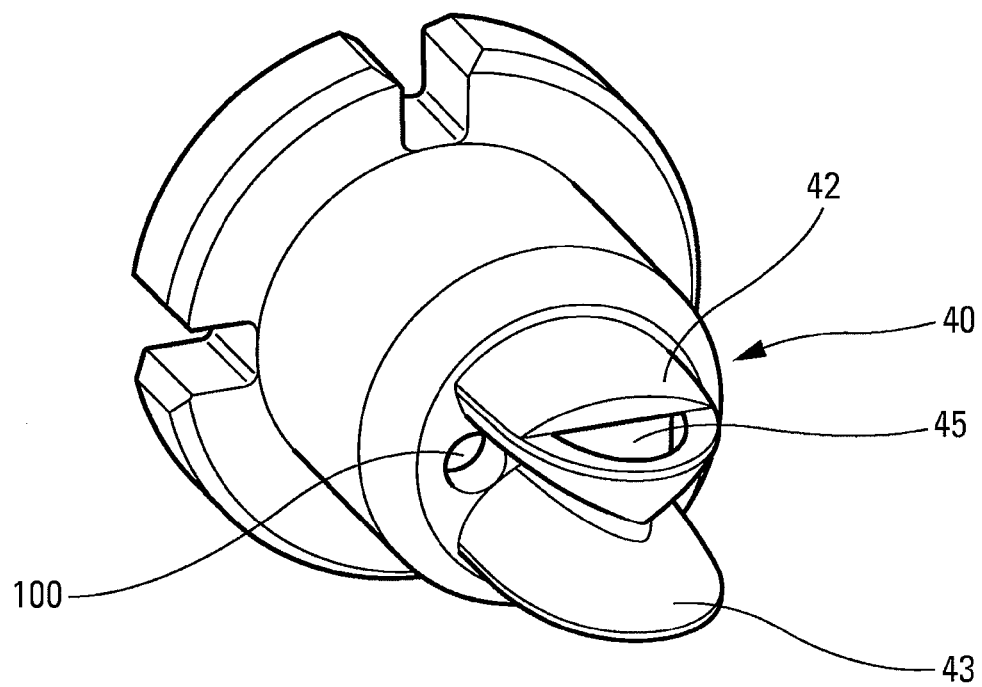
FIG. 1 is a diagrammatic perspective view of a perforator element constituting an embodiment of the present invention.
Figure 2:
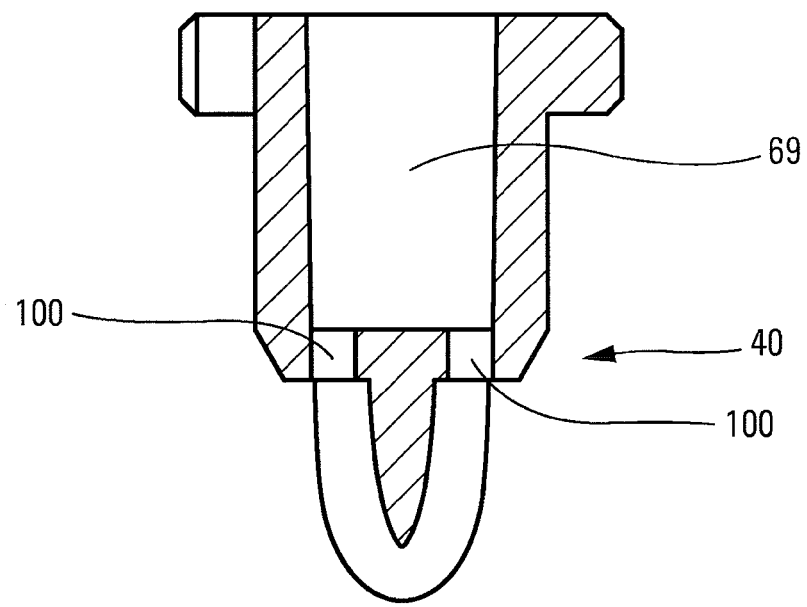
FIG. 2 is a cross-section view of the FIG. 1 perforator element.
Figure 3:
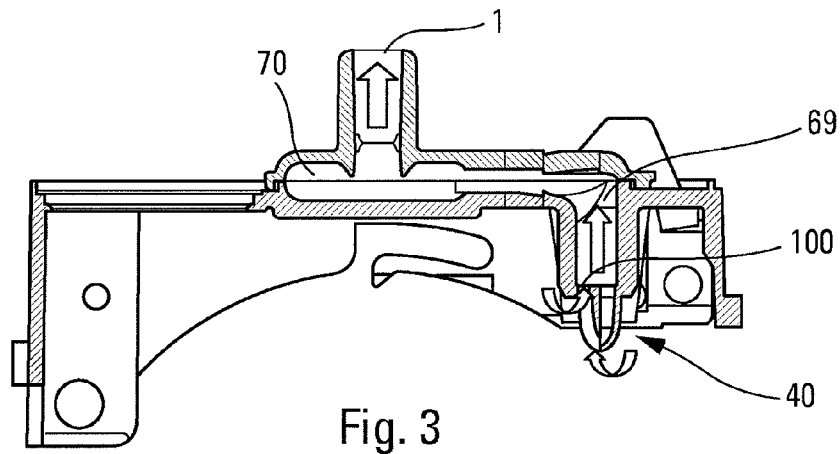
FIG. 3 is a cross-section view of a portion of an inhaler including a perforator element as shown in FIGS. 1 and 2.

The air channel 100 can be rectilinear, parallel to said expulsion channel 69, and of cross-section that is constant, as shown in FIGS. 1 to 3. In a variant, it could be of any shape, of section that varies, e.g. frustoconical, as a function of the desired effects when it mixes with the air and powder flow in the expulsion channel 69.

Advantageously, said at least one air channel 100 is made in a wall of the perforator element 40, which wall does not penetrate into the blister 20, preferably a wall that is substantially perpendicular to the expulsion channel 69, as shown in FIGS. 1 to 3. Each air channel 100 is thus made by a through hole made in a wall of the perforator element 40, said through hole being oriented substantially parallel to said expulsion channel. This configuration makes it possible to obtain a maximum effect with the air flow oriented in the same direction as the air and powder flow.

The perforator means 40 preferably have an appropriate shape, such that the cut wall-portions of the blister 20 fold towards the inside of the blister without covering the openings formed by the perforator means 40. Advantageously, the perforator means 40 include at least two opposite perforator ends 42, 43 that are spaced apart from each other by an appropriate distance 44. The perforator means 40 advantageously create a central fold in the cut wall-portions, making it possible to ensure that the openings that are formed are not at all covered by any cut wall-portion. Advantageously, as shown in FIG. 1, each perforator end 42, 43 is cup shaped, said cups being disposed back to back and having sharp edges. Advantageously, the incoming air (arrow A) penetrates into the open blister by passing over the outside of said perforator means 40. By way of example, this can be obtained as a result of the blisters 20 moving towards their opening position along a curved line. The movement along a curve results in one or more openings that are slightly larger than the outside dimensions of the perforator element 40. Therefore, this enables the inhalation air to flow over the outside of said perforator element 40 in order to penetrate into the blister. If necessary, special means could also be provided for forming an opening outside said perforator element 40, e.g. projections 41 or any other appropriate external profile on said perforator element 40 (see FIG. 6). Preferably, the flow of outgoing air carrying powder (arrow A) leaves the blister 21 by passing into said hollow perforator means 40, as shown in FIGS. 3 to 6. The specific shape of the perforator element 40 as shown in the figures provides a "louvre" type cut that provides all of the advantages mentioned above, and in particular avoids the holes, that are created by perforating, being covered, even in part, by perforated wall portions. This makes it possible to guarantee that the blister is emptied as completely as possible, and thus ensures that the dispenser is as effective as possible. In addition, metering reproducibility is good, with the same quantity of powder being expelled each time by means of the device of the invention. Preferably, the perforator element 40 includes two air channels 100 that are disposed symmetrically between the two perforator ends 42, 43, as shown in FIGS. 1 to 3. Naturally, any number of air channels 100, possibly of dimensions that are different to one another, could also be envisaged.

Advantageously, while the reservoir 20 is moving towards its opening position in order to be opened by the perforator means, the perforator means 40 preferably do not move relative to the body of the inhaler. However, it is possible to envisage that the perforator means could also move during the step of opening the reservoir. For example, the perforator means could be moved towards the reservoir while the reservoir is being moved towards the perforator means. In another variant, it is also possible to envisage that the reservoir and the perforator means are moved in the same direction during actuation, the reservoir being moved more quickly in said direction, such that it comes into contact with said perforator means in order to be opened.

The inhaler further includes a dispenser chamber 70 for receiving the dose of powder after a respective reservoir has been opened. Advantageously, the dispenser chamber 70 is provided with at least one bead (not shown) that moves inside said chamber 70 during inhalation so as to improve the dispensing of the air and powder mixture after a reservoir has been opened, in order to increase the effectiveness of the device.

As shown in the figures, it can be advantageous for the opening means, in particular for the perforator means 40, to be formed directly on said dispenser chamber 70, e.g. at the end of a channel 69, forming an expulsion channel leading to said chamber 70.

Advantageously, the individual reservoirs or blisters 20 are formed on an elongate strip (not shown) that can be stored in the form of a roll inside the body of the inhaler. The blister strip can be moved by the user, advantageously by means of the indexer wheel (not shown) that advantageously includes at least one and preferably more recesses having a shape that corresponds substantially to the shape of the blisters. Thus, when the indexer wheel turns, it drives the blister strip. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

Various modifications can also be envisaged by a person skilled in the art, without going beyond the ambit of the present invention, as defined by the accompanying claims.

The invention claimed is:

1. An inhaler device comprising an opening device for opening an individual reservoir containing a single dose of powder, said reservoir including a closure wall, said opening device comprising hollow perforator means that are adapted to perforate said closure wall of the reservoir, said hollow perforator means being connected to an expulsion channel that, in turn, is connected to and in communication with a dispenser chamber for receiving the dose of powder after the reservoir has been opened and prior to delivering the dose of powder to a dispenser orifice of said inhaler, said opening device including at least one air channel connected to said expulsion channel, such that during inhalation, an air flow passing through said at least one air channel mixes, in said expulsion channel, with the air and powder flow leaving the reservoir through said hollow perforator means, said at least one air channel is formed by a through hole made in a wall of said perforator means, said at least one through hole being oriented substantially parallel to said expulsion channel and said at least one air channel formed in a wall of said perforator means that is perpendicular to said expulsion channel, such that said air flow is oriented in the same direction as said air and powder flow; said perforator means formed at an end of the expulsion channel; wherein the opening device is fixed so as not to move relative to the body of the inhaler while the reservoir is being opened; the reservoirs are made in the form of an elongate strip comprising a plurality of individual reservoirs disposed one behind another.

2. A device according to claim 1, wherein said at least one air channel is made in a wall of the perforator means that does not penetrate into the reservoir.

3. A device according to claim 1, wherein said at least one air channel is substantially rectilinear.

4. A device according to claim 1, wherein said at least one air channel has a section that is substantially constant along its length.

5. A device according to claim 1, wherein said at least one air channel has a section that varies along its length.

6. A device according to any preceding claim, wherein said perforator means include two opposite perforator ends that are spaced apart by a distance.

7. A device according to claim 6, wherein said perforator means include two air channels that are disposed symmetrically between said two perforator ends.

8. A device according to claim 1, wherein the flow of incoming air penetrates into the open reservoir by passing over the outside of said perforator means.

9. A device according to claim 8, wherein said perforator means include at least one external projection so as to form at least one passage for the incoming air entering into the open reservoir.

10. The device according to claim 9, wherein said at least one external projection is a spline.

11. A device according to claim 1, wherein said opening device is activated by the user inhaling.

12. A device according to claim 11, wherein during inhalation, a reservoir is moved against said opening device, such that said reservoir is opened while a first inhalation flow enters into the reservoir by passing over the outside of said perforator means, causing the fluid to be expelled towards the expulsion channel by passing into said perforator means, said first inhalation flow mixing, in the expulsion channel, with a second inhalation flow passing through said at least one air channel.

13. An inhaler device comprising an opening device for opening an individual reservoir containing a single dose of powder, said reservoir including a closure wall, said opening device comprising a hollow perforator adapted to perforate said closure wall of the reservoir, said hollow perforator connected to an expulsion channel so as to transport the powder towards a dispenser orifice of said inhaler, said opening device including at least one air channel connected to said expulsion channel, such that during inhalation, an air flow passing through said at least one air channel mixes, in said expulsion channel, with air and powder flow leaving the reservoir through said hollow perforator, said at least one air channel is formed by a through hole made in a wall of said perforator, said at least one through hole oriented substantially parallel to said expulsion channel, said at least one air channel formed in a wall of said perforator that is perpendicular to said expulsion channel, such that said air flow is oriented in the same direction as said air and powder flow, and said opening device configured to be activated by airflow generated by inhalation through the dispenser orifice.

* * * * *